United States Patent

Roy

Patent Number: 5,549,682
Date of Patent: Aug. 27, 1996

[54] SHOULDER JOINT PROSTHESIS WITH ANGULAR ADJUSTMENT

[76] Inventor: Stephen C. Roy, 1425 E. Newport Center Dr., Deerfield Beach, Fla. 33442

[21] Appl. No.: 261,335

[22] Filed: Jun. 16, 1994

[51] Int. Cl.⁶ .................................. A61F 2/40; A61F 2/30
[52] U.S. Cl. .................................. 623/19; 623/18
[58] Field of Search .................................. 623/19, 20, 21, 623/22, 18

[56] References Cited

U.S. PATENT DOCUMENTS

| | | | |
|---|---|---|---|
| 4,919,670 | 4/1990 | Dale et al. | 623/19 |
| 5,002,577 | 3/1991 | Bolesky et al. | 623/22 |
| 5,314,479 | 5/1994 | Rockwood, Jr. et al. | 623/19 |
| 5,358,526 | 10/1994 | Tornier | 623/19 |
| 5,387,241 | 2/1995 | Hayes | 623/20 |

*Primary Examiner*—Debra S. Brittingham

[57] ABSTRACT

A shoulder joint prosthesis system comprising a stem and a plurality of heads, the stem defining a head receiving surface lying at an angle of greater than zero and less than 40 degrees relative to the stem and each of the heads defining a generally spherical articulation surface having a radius of curvature and mounting means for mounting the head on the stem, the mounting means having an axis of rotation of the head, the axis of rotation and the radius of curvature lying at an angle of greater than zero and less than 40 degrees to each other is disclosed.

4 Claims, 2 Drawing Sheets

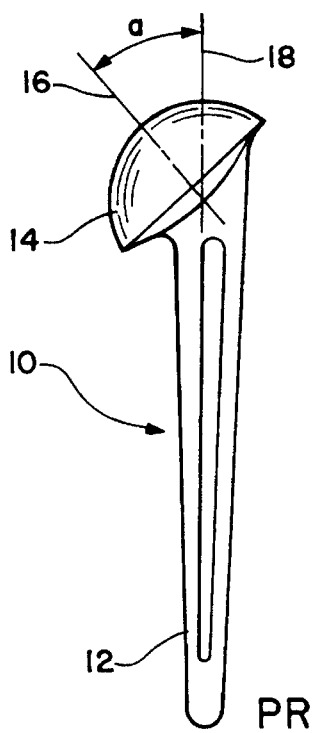
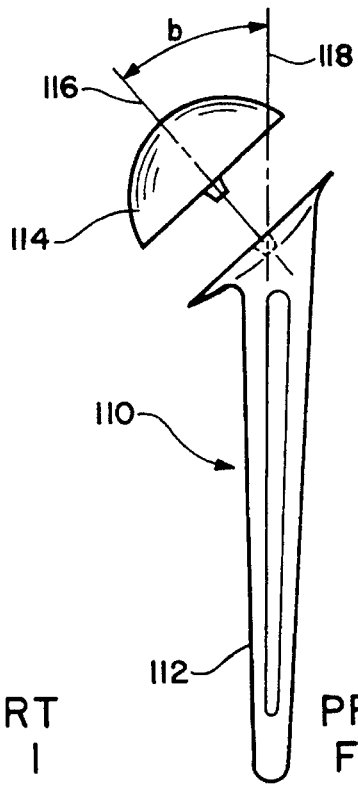
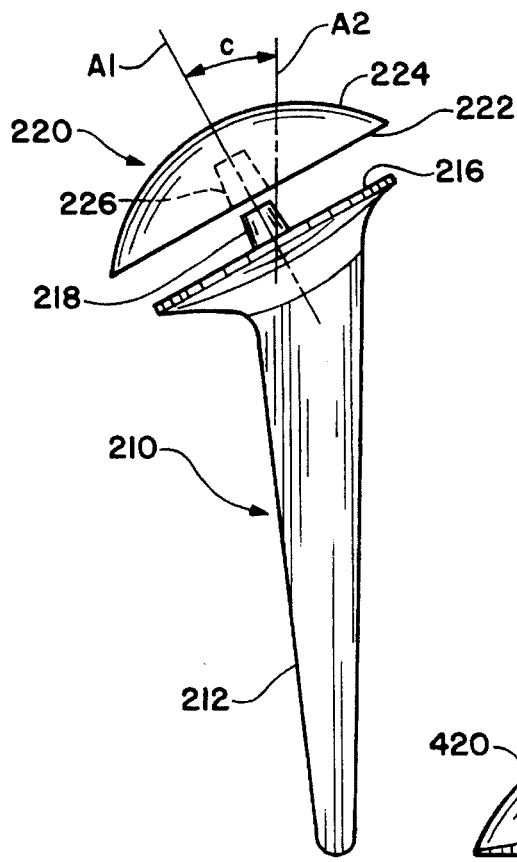
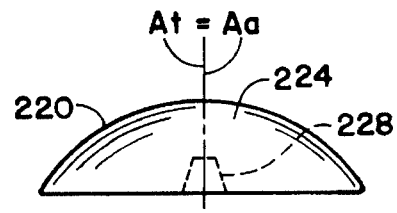
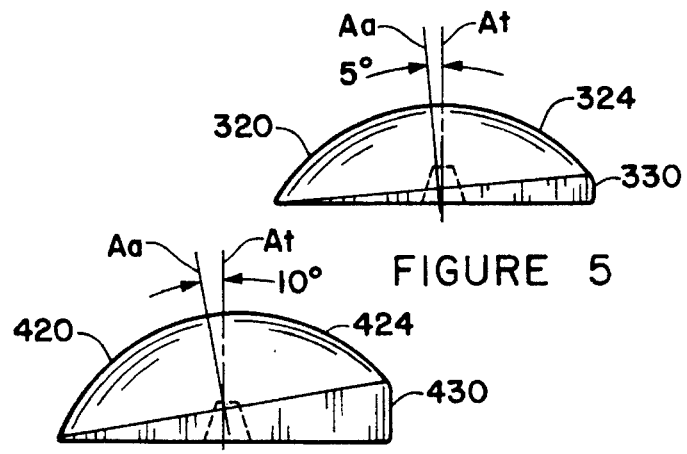
PRIOR ART FIGURE 1
PRIOR ART FIGURE 2
FIGURE 3
FIGURE 4
FIGURE 5
FIGURE 6

SHOULDER JOINT PROSTHESIS WITH ANGULAR ADJUSTMENT

FIELD OF THE INVENTION

This invention relates to shoulder joint prosthesis and, more particularly, to prosthesis for replacing the ball portion of the shoulder joint.

BACKGROUND OF THE INVENTION

Shoulder implant prostheses generally consist of a "head" portion of the implant which articulates with the natural or artificial glenoid surface, and a "stem" portion of the implant which provides fixation within the humeral canal. Early shoulder implants were unitary structures, being an integral structure combining the stem and the head. A device of this type is depicted in FIG. 1. Shoulder implant designs become modular in the late 1980's. A modular device generally exemplary of these prosthesis is shown in FIG. 2. These modular implants were characterized in that the head independently mated via "taper-lock" connection to the humeral stem. This modularity increased the options for the surgeon by offering significantly more sizes of heads, e.g. ten to twenty heads instead of the three to six heads available in earlier non-modular prostheses and more stems, e.g. five to ten instead of the two to four sizes of stems available in non-modular prostheses.

This modularity decreased the actual number of parts required to meet the various requirements the surgeon might face in installing such prosthetic devices. For example, with five modular stems and ten modular heads the surgeon had flay size options with only fifteen parts. Conversely, a non-modular system offering the same choices would require fifty prostheses.

Modular taper-lock connections of the head to the stem are well-known in the art[vary slightly in design]. In general, taper-lock connections comprise a tapered pin, e.g. a frustoconical pin, and a tapered receptacle that is configured to receive the pin generally but wherein there is a difference in the taper of the pin and the taper of the of the receptacle such that upon substantially full insertion the tapered pin locks into the receptacle, thereby preventing rotation of the pin in the receptacle. Such a structure is used in the present invention. It will be immediately apparent that the pin and the receptacle, respectively, can be formed in or as part of either the head or the stem, the two forms of taper lock being perfectly equivalent.

The heads of all prior art modular shoulder prostheses have incorporated a sphere or semi-spherical geometry with a male or female taper which is disposed at an angle of 90 degrees relative to the articulating surface of the head and an angle of 90 degrees relative to the undersurface of the head. This results in a fixed position of the head relative to the stem placement within the humeral canal. Once the humeral canal is prepared to accept the stem, the head is locked into the stem resulting in the fixed position. The only way to change the head position thereafter is to re-prepare the humeral canal for repositioning of the stem. This rearrangement is usually not possible due to anatomical restraints.

A principal feature of the present invention is that a shoulder prosthesis is provided that permits angular adjustment of the head relative to the stem.

SUMMARY OF THE INVENTION

The present invention provides an improved modular shoulder joint prosthesis that comprises a stem and a head for being mounted on the stem. The improved prosthesis comprises a stem that is configured and constructed to define a generally planar head receiving surface and a head that comprises a body formed and configured to define an articulation surface generally in the shape of a spherical segment for being received in and articulating in a socket in a patient's shoulder, a stem engaging surface constructed and configured to lie adjacent and rotate relative to the head receiving surface on the stem and a wedge segment portion between the spherical segment portion and the stem engaging surface for disposing the articulation surface at an angle of from about five greater than zero and less than about thirty degrees from the plane of the head engaging surface of the stem when the head is position thereon.

The head and stem, respectively, define, in a preferred embodiment, a frustoconical pin having a tapered outer surface and a recess having tapered walls for receiving the frustoconical pin, the taper of the walls and the taper of the outer surface of the pin form an contact, press or interference fit to lock the head from rotation relative to the stem when the head is pressed toward the head receiving surface of the stem.

A shoulder joint prosthesis comprising a stem and a head is provided such that the stem is so constructed and configured as to define an elongate portion for being received in the humeral canal of a patient and a head receiving surface, the head receiving surface lying at an angle of greater than zero and less than 40 degrees relative to the elongate portion, the head comprising a body defining an articulation surface generally in the form of a spherical segment having a radius of curvature, the articulation surface defining an articulation axis Aa approximately centrally thereof along the radius of curvature of the articulation surface, a stem engaging surface adapted and constructed to lie adjacent and rotate on the head receiving surface of the stem, and generally frustoconical structure defining the axis of rotation At of the head on the stem, and a generally wedge shaped portion between the spherical segment portion and the stem engaging surface disposing the axis of articulation Aa at an angle of greater than zero and less than about 30 degrees from the angle of rotation At.

Again, in a preferred embodiment, the head and stem, respectively, define a frustoconical pin having a tapered outer surface and a recess having tapered walls for receiving the frustoconical pin, the taper of the walls and the taper of the outer surface of the pin form an contact, press or interference fit to lock the head from rotation relative to the stem when the head is pressed toward the head receiving surface of the stem.

The invention is embodied also in a shoulder joint prosthesis system comprising a stem and a plurality of heads, the stem being so constructed and configured as to define an elongate portion for being received in the humeral canal of a patient and a head receiving surface, the head receiving surface lying at an angle of greater than zero and less than 40 degrees relative to the elongate portion, each of the heads comprising a body defining an articulation surface generally in the form of a spherical segment having a radius of curvature, the articulation surface defining an articulation axis Aa approximately centrally thereof along the radius of curvature of the articulation surface, a stem engaging surface adapted and constructed to lie adjacent and rotate on the head receiving surface of the stem, and generally frustoconical structure defining the axis of rotation At of the head on the stem, and a generally wedge shaped portion between the spherical segment portion and the stem engaging surface disposing the axis of articulation Aa at an angle of greater than zero and less than about 30 degrees from the angle of rotation At, the generally wedge shaped portions in the respective heads being so constructed and configured as to dispose the axis of articulation Aa the respective heads at different angles of greater than zero and less than about 30 degrees of the angle of rotation At.

BRIEF DESCRIPTION OF THE DRAWINGS

FIG. 1 depicts an exemplary configuration of a unitary Prior Art shoulder joint prosthesis that preceded the present invention.

FIG. 2 depicts an exemplary configuration of a modular Prior Art shoulder joint prosthesis that preceded the present invention.

FIG. 3 depicts a side elevational, exploded view of the stem that includes a frustoconical tapered pin, sometimes referred to hereinafter by the abbreviation "taper", and a symmetrical head of the type known in the prior art.

FIGS. 4, 5, 6, 7 and 8, depict heads that form a frustoconical recess that is configured and dimensioned to receive the taper in a "taper lock" fit such that the taper frictionally engages the walls of the recess to prevent rotation of the head when the taper is fully inserted in the recess, and wherein:

FIG. 4 is a symmetrical head provided for comparison purposes;

FIG. 5 is an asymmetrical head of the present invention having a 5° angle between the axis of articulation,. Aa, and the axis of the taper, At.

FIG. 6 is an asymmetrical head of the present invention having a 10° angle between the axis of articulation,. Aa, and the axis of the taper, At.

FIG. 7 is an asymmetrical head of the present invention having a 15° angle between the axis of articulation,. Aa, and the axis of the taper, At.

FIG. 8 is an asymmetrical head of the present invention having a 20° angle between the axis of articulation,. Aa, and the axis of the taper, At.

DESCRIPTION OF THE PREFERRED EMBODIMENT

Figure 7:
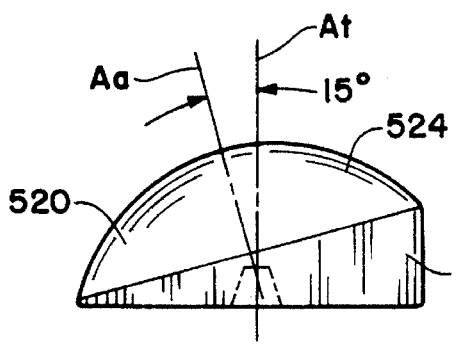

For comparison purposes and background understanding, reference is first made to FIG. 1 through 4.

Early prior art shoulder joint prosthesis 10 comprised in a unitary structure a stem 12, adapted and dimensioned to be inserted in the patients humeral canal, a head 14 oriented at a predetermined angle a relative to the axis of articulation of the joint and the axis of the stem. Reference is made to the axis of the stem recognizing that the stem may or may not be symmetrical and, therefore, in the strict mathematical sense may not have a true axis; however, the stem will be fitted into the patient's humeral canal, which is in a general sense a calendar, generally along the axis of the humeral canal and, hence, generally along an imaginary line extending longitudinally through the central portion of the stem. A line 18 parallel to that center line is shown in FIG. 1 to define the angle a.

The prior art shoulder joint prosthesis 110 comprised in a modular structure comprising a stem 12, adapted and dimensioned to be inserted in the patients humeral canal, and a removable head 114 oriented at a predetermined angle b relative to the axis of articulation of the joint and the axis of the stem. Again, reference is made to the axis of the stem recognizing that the stem may or may not be symmetrical and, therefore, in the strict mathematical sense may not have a true axis; however, the stem will be fitted into the patient's humeral canal, which is in a general sense a calendar, generally along the axis of the humeral canal and, hence, generally along an imaginary line extending longitudinally through the central portion of the stem. A line 118 parallel to that center line is shown in FIG. 1 to define the angle b.

In FIGS. 2 the recess is formed in the stem and the taper is formed in the head. In a perfectly equivalent reversal of parts, FIG. 3 depicts a stem, which is used to illustrate the present invention as well as the prior art, which has formed thereon the taper and a head in which the recess is formed. The stem 210 has an elongate portion 212 that is equivalent to portions 12 and 112 of FIGS. 1 and 2 respectively, and which is constructed and dimensioned to be received in the patients humeral canal. The distal portion of the stem 210 is constructed and configured to define a head receiving surface 216 on which is formed a taper 218, i.e. a frustoconical pin, the longitudinal surface of which tapers inwardly from the base to the top. The head 220 is a body formed and constructed to define a surface 224 that is generally in the form of a spherical segment symmetrically disposed about an axis of articulation of the joint, identified as A1 in FIG. 3. A1 is also the axis of the taper 218. The head also defines a stem engaging surface 222 that is configured to lie adjacent the head engaging surface 216 on the stem 210. The surfaces 216 and 222 may be, and most simply manufactured are, flat surfaces; however, mated frustoconical surfaces, mated arcuate surfaces, etc. may be used. These surfaces are preferably approximately the same size but need not be. For example, the surface 222 may comprise a portion forming the mating surface and a portion extending outwardly therefrom and either downwardly or otherwise if desired. The angle c between the axis of the taper and axis of articulation, both lying on the axis A1 and the axis of the stem A2 is generally about 30°±5°, however, this is not a critical angle because the present invention provides great flexibility for adjusting the angle of articulation. If desired, a set of two or three stems with different angles c may be provided, but is not usually necessary.

Again for comparison and understanding, the head 220 is illustrated in FIG. 4. It will be noted that the axis of articulation Aa and the angle of taper At lie on the same line. A plurality of heads having different diameters can be provided in a shoulder prosthesis system to permit the surgeon to select a head having the appropriate size; however, no angular adjustment is permitted.

Reference will now be made to FIGS. 5, 6, 7 and 8 which depict heads of the present invention. The heads of FIGS. 5, 6, 7 and 8 are identical in size, i.e. radius of curvature of the articulation surface, the spherical segment that articulates in the patients natural or prosthetic shoulder socket, it being clearly contemplated that a shoulder prosthesis system comprising the present invention would normally include, typically, four to six sizes of head having the angular relationships described below.

Referring now to FIG. 5, head 320 comprises an articulation surface 322 of the same size, i.e. radius of curvature of the spherical segment defining said surface, as the surface 224 shown in FIG. 4; however, the head 320 further comprises an angle fixing wedge segment 330 that fixes the angle of articulation Aa at a predetermined angle from the angle of taper At, such angle being referred to for convenience as angle Aa<>At. In FIG. 5, the angle Aa<>At is 5°

Referring now to FIG. 6, head 420 comprises an articulation surface 422 of the same size as the surface 224 shown in FIG. 4; however, the head 420 further comprises an angle fixing wedge segment 430 that fixes the angle of articulation Aa at a predetermined angle from the angle of taper At, such angle being referred to for convenience as angle Aa<>At. In FIG. 5, the angle Aa<>At is 10°.

Referring now to FIG. 7, head 520 comprises an articulation surface 522 of the same size as the surface 224 shown in FIG. 4; however, the head 520 further comprises an angle fixing wedge segment 530 that fixes the angle of articulation Aa at a predetermined angle from the angle of taper At, such angle being referred to for convenience as angle Aa<>At. In FIG. 7, the angle Aa<>At is 15°.

Figure 8:
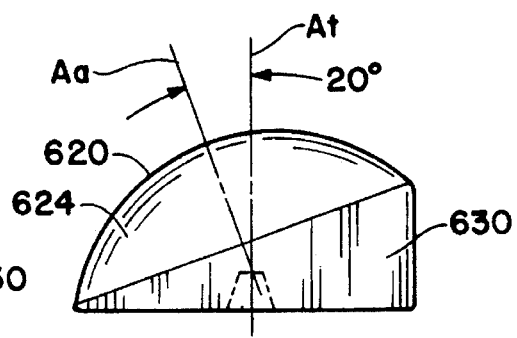

Referring now to FIG. 8, head 620 comprises an articulation surface 622 of the same size as the surface 224 shown in FIG. 4; however, the head 620 further comprises an angle fixing wedge segment 630 that fixes the angle of articulation Aa at a predetermined angle from the angle of taper At, such angle being referred to for convenience as angle Aa<>At. In FIG. 8, the angle Aa<>At is 20°.

Figure 9:
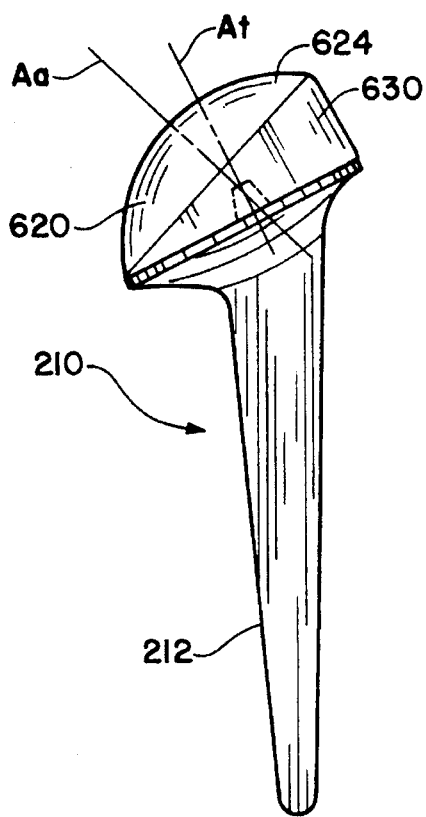
FIG. 9 depicts the shoulder ball prosthesis of this invention having the asymmetrical head depicted in FIG. 8 fitted thereon oriented to obtain the maximum angle of articulation relative to the axis of the stem.
Figure 10:
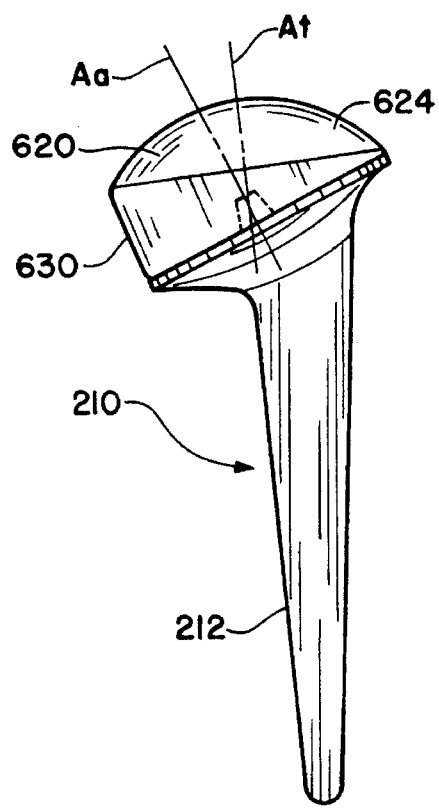
FIG. 10 depicts the shoulder ball prosthesis of this invention having the asymmetrical head depicted in FIG. 8 fitted thereon oriented to obtain the minimum angle of articulation relative to the axis of the stem, FIG. 10 being the exact same structure as depicted in FIG. 9 but with the head rotated 180° relative to the position of the head in FIG. 9.

Reference is now made to FIGS. 9 and 10, that depict the same mechanical structure but with the head being shown in different positions on the stem. In FIG. 9, the head 620 is rotated on the stem head receiving surface and taper to obtain the maximum angular orientation relative to the axis of the stem. In FIG. 10, the head 620 is rotated on the stem head receiving surface and taper to obtain the minimum angular orientation relative to the axis of the stem. Any angular orientation between that shown in FIG. 9 and that shown in FIG. 10 can be obtained simply by rotating the head on the stem.

Figure 11:
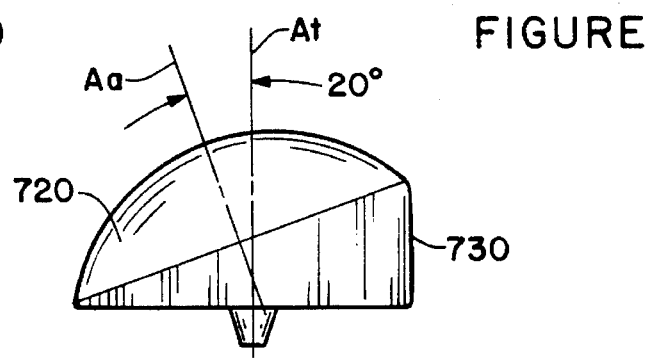
FIG. 11 depicts an equivalent alternative head wherein the taper is formed on the head and fits with a recess in the stem, such as appears in FIG. 2.

FIG. 11 simply illustrates the equivalency of heads having the taper on the head that fit into a recess in the stem with the heads as depicted in FIGS. 5 through 8. The head 720 defines a surface of articulation having an axis of articulation Aa disposed at 20° to the axis of taper At, the taper, in this embodiment, being on the head.

Once the optimum head size and angular orientation are determined, the surgeon simply presses the head toward the stem, inserting the taper fully into the recess. The frustoconical structure, referred to as the "taper", is the same size as the recess, i.e. the radius of the circle defined by the surface of the frustocone from the center axis is the same at a series of points as the circle defined by the surface of the recess from the center of the recess at a corresponding set of points. Hence, when the taper is fully inserted in the recess the taper forms a contact or press fit with the surface of the recess. This results in a locking relationship between the taper and the recess preventing rotation of the ball on the stem. This type of taper lock is known in the art. Other locking arrangements that will prevent relative rotation of the head and the stem may be used. In the present invention, the male or female taper connection is offset varying degrees from the articulating surface. This allows the surgeon to place and lock the head into infinite number of positions within the humeral stem, which has previously been positioned, thus varying the articulating face of the head into an infinite number of positions. For instance, a 20 degree offset head, e.g. as depicted in FIG. 8, will change the face angle up to 40 degrees if the thickest portion of the head is rotated 180 degrees from its original placement. The thickest portion of the offset head can be placed infinitely, therefore the face angle may be changed from 20 degrees in one position to 20 degrees in the opposite position, or any position in between, thus resulting in the infinite number of positions.

A shoulder joint prosthesis system will typically contain a plurality of heads with varying degree offsets from 0 degree, non-offset, to 20 degree offset, typically offsets of 5, 10, 15 and 20 degrees may be included; however, any degrees of offset may also be included.

The resulting benefit of the asymmetrical shoulder joint prosthesis of this invention is the ability for the surgeon to intraoperatively vary the articulation of the humeral head with the natural or artificial glenoid surface. This variability can be achieved independent of the humeral implant position. This could provide the patient with improved biomechanics and improved function of the artificial joint.

A secondary benefit is that a surgeon may change the articulating position in cases of re-operation, due to instability or unsatisfactory range of motion, by simple head removal and repositioning of the offset head at a more desirable position. In order to change the head position of "non-offset" heads, the difficult task of stem removal and repositioning of the stem within the humeral canal (if possible) would be necessary.

In general, the same surgical techniques used for implanting other shoulder joint prosthesis may be used for the present invention. The method of using the invention described below is, therefore, merely exemplary and not limiting.

Proper x-rays are obtained of the proximal humerus. Templates may be used for preoperative assessment of implant fit. Standard surgical prep is utilized as in any joint replacement surgery. Special attention to prep in axilla is recommended. The patient is placed in a 30° raised ("beach chair") position with the head secured on a Mayfield headrest. A foam pad is placed under the scapula. The involved shoulder is positioned so it extends off the table free to manipulate during the procedure.

An anterolateral incision is made beginning at the clavicle over the coracoid should extend 12–15 cm along the deltopectoral groove just lateral to the axillary crease. The surgeon locates and exposes the cephalic vein laterally with the deltoid origin from the clavicle. Generally, the vein is retracted laterally with the deltoid, however certain circumstances may dictate medial retraction with the pectoralis. The cephalic vein is quite fragile and care must be exercised when retracting. The deltoid is freed from deep underlying tissues from its origin on the clavicle, care being taken to avoid releasing from clavicle, to its distal insertion on the humerus. Occasionally it may be necessary to partially release the deltoid from the humerus. Once the anterior structures are exposed, the upper 1 cm portion of the pectoralis major tendon is incised with a cautery knife. It is not necessary to repair the pectoralis major. The scapularis tendon may be incised 1.5 cm from its insertion perpendicular to its fibers. Areas in which bleeding occurs are cauterized and tagged with sutures for subsequent repair.

In cases with significant restriction in external rotation, a subscapularis Z-plasty is performed to lengthen the tendon and increase range of motion. After the subscapularis tendon has been released, any adhesions evident at the coracoid process and the anterior glenoid rim are dissected. A partial (50%) vertical incision is made through the subscapularis into a coronal Z. A complete dissection around the border is necessary for a function lengthening. This will require extensive tissue dissection down to the level of the lesser tuberosity and anterior aspect of the scapular neck. Subperiosteal dissection is required to protect the axillary nerve. Repair is with a heavy nonabsorbable suture. A capsule is included with the repair to enhance the strength.

The arm is externally rotated and abducted and the deltoid is gently retracted laterally and cojoined tendon medially with Richardson retractors. It is important to identify and protect the musculocutaneous and axillary nerves within the medial aspect of the cojoined tendon. An elevator is placed under the capsule to protect against damage to the nerves. The capsule is incised just medial to the lesser tuberosity and released from its attachment on the humerus to inferior border. Further external rotation and abduction of the arm will expose the humeral head.

The lesser tuberosity is retracted with a blunt retractor in order to obtain adequate exposure to the humeral head for ANTERIOR fracture/dislocations. The greater tuberosity is retracted to obtain exposure for POSTERIOR fracture/dislocations.

The humeral head is retracted by sliding a small Darrach retractor posterior under the biceps to protect the structures during resection to the head. The head is osteotomized utilizing the resection template, paying careful attention to proper alignment (varus/valgus & 35–40 of retroversion). Resection level is conservative since a secondary planing process can determine the final seating level.

The starter reamer is manually inserted, paying careful attention to axial alignment, and the humeral canal is progressively reamed by hand or power up to the desired size based on preoperative templating and intraoperative assessment. The cemented size on the reamer provides a "line-to-line" fit. The humeral canal is progressively broach beginning with at least two sizes smaller than the intended final size. The broach is aligned in 30 to 40 of retroversion. When the final broach is inserted to the desired depth, the handle is removed and the planer may be used to precision machine the osteotomy for an intimate fit with the collar on the stem. A trial head is placed on the broach for trial reduction and preliminary head sizing. A final trial assessment may be performed after the humeral prosthesis is implanted.

Proper modern cementing techniques are utilized. The canal is bristle brushed followed by thorough pulsed irrigation. A cement restrictor is inserted to at least 2 cm distal to the stem. The canal is dried with a wick or using any other appropriate method. The humeral implant stem is opened and passed into the sterile field. The cement is inserted with a cement gun in a retrograde fashion. The humeral implant stem is inserted paying careful attention to orientation (neutral varus/valgus and 35–40 of retroversion). Excess cement trimmed and the stem is held motionless until cement the hardens.

Once the canal has been prepared for a press-fit application, the humeral implant is opened and passed into the sterile field. The stem is inserted digitally paying careful attention to proper orientation (neutral varus/valgus and 35–40 of retroversion). The stem driver is used to seat the stem to the predetermined position.

Once the humeral stem is implanted, a trial head can be placed on the implant for final assessment for fit, range of motion, and soft tissue balance. The greater and lesser tuberosities are reduced to ensure that the cuff is balanced. Once the head size is determined, the modular head implant is opened and passed into the sterile field. The taper connections on the stem and modular head are inspected, cleaned, and thoroughly dried prior to assembly. The head is impacted with the head impactor and checked to ensure that it is fully seated and locked.

Heavy non-absorbable suture, 18 gauge cobalt chrome wire, or 1.6 mm cobalt chrome cable, or comparable device, may be used for cerclage attachment of the greater and lesser tuberosity to the lateral and/or medial aspect of the stem. The cable, or a suture or wire, is passed through the tendon near the top of the greater tuberosity then through one of the proximal holes in the lateral fin of the stem. Another cable, or suture or wire, is passed through the tendon or bone in the central aspect of the greater tuberosity into the central hole in the fin. The initial cable, or suture or wire, is passed through the upper part of the scapularis tendon on the lessor tuberosity and the second through the subscapularis or lesser tuberosity. A 2.7 mm drill is used to pass the cerclage through the lateral cortices of the humeral shaft to securely attach the tuberosities to the shaft. The cable, or suture or wire, is tensioned and each fragment is reduced to the anatomical position making sure they are distal to the articulating head of the implant. The cable, or suture or wire, is tightened and secured in the usual manner. Rotator cuff tears are advanced and repaired to avoid range of motion complications.

The interval between the capsule and the subscapularis us repaired anatomically with non-absorbable suture and a closed wound drainage tube is inserted between the rotator cuff and the deltoid, paying careful attention to avoiding the axillary artery. The deltopectoral interval is closed with 2-0 absorbable suture and the skin is closed in the usual manner. The wound is dressed in the usual manner and a "sling & swathe" is applied for postoperative immobilization.

The patient should be instructed about the restricted activities while the fracture and soft tissues are healing. It is extremely important to follow a comprehensive rehabilitation exercise program for optimal long term results.

The invention is embodied in its most essential form in a head for a shoulder implant prosthesis system that comprises a stem, the head comprising a body defining an articulation surface in the form of a spherical segment adapted to be received in the shoulder socket of a patient, the head also formed to define a stem mating surface and a frustoconical recess in such surface and a wedge segment portion between the spherical segment portion and the stem mating surface for disposing the axis of articulation of the spherical segment, generally defined by the center of the spherical segment and the radius of curvature thereof, and the axis of the recess.

An alternate and identically equivalent structure may comprise a frustoconical pin, referred to as a "taper", formed on and extending from the stem engaging surface, the stem defining a recess for receiving the taper. In this form, the wedge segment portion between the spherical segment portion and the stem mating surface disposes the axis of articulation of the spherical segment, generally defined by the center of the spherical segment and the radius of curvature thereof, at an angle relative to the axis of the taper.

In another embodiment, the invention comprises at least one stem adapted and constructed to be inserted in the patients humeral canal and defining a head engaging surface and a plurality of heads, each of which is adapted to be received on said stem and being rotatable thereon, interengaging means on each of the respective heads and, respectively, on the stem for selectively permitting rotation of the head on the stem and for locking the head from rotation on the stem. The interengaging means are preferable a taper on a recess, one being formed on the head and the other on the stem, so constructed and configured that when the taper is fitted into the recess the surface of the taper engages the walls off the recess to prevent rotation of the head.

It will be appreciated that the drawings and description are exemplary of the preferred embodiment and not limiting of the invention.

Industrial Application

The invention is useful in the medical appliance industry and in surgery.

What is claimed is:

1. In a modular shoulder joint prosthesis that comprises a stem and a head for being mounted on the stem, the prosthesis comprising:

(a) a stem configured and constructed to define a generally planar head receiving surface; and (b) a head consisting of a single unitary discoid body having first and second sides, a generally spherical segment shaped articulation surface for being received in and articulating in a socket in a patient's shoulder, said segment defining said first side surface of said discoid body, a generally planar stem engaging surface constructed and configured to lie adjacent the head receiving surface on the stem, the stem engaging surface and the head receiving surface lying generally in the same plane and being rotatable relative to each other, said stem engaging surface defining the second side of said discoid body, said first and second sides of the discoid body being spaced from each other by a central portion that defines a discoid circumference having a diameter, the central portion being generally wedge shaped for disposing the articulation surface at an angle of from about five degrees or greater and less than about thirty degrees from the plane in which the head receiving surface of the stem lies when the head is positioned thereon.

2. The prosthesis of claim 1 wherein the stem defines a frustoconical pin having a tapered outer surface and the head defines a recess having tapered walls for receiving the frustoconical pin, the taper of the walls and the taper of the outer surface of the pin form an interference fit to lock the head from rotation relative to the stem when the head is pressed toward the head receiving surface of the stem.

3. A shoulder joint prosthesis system comprising a stem and a plurality of heads, the stem being so constructed and configured as to define an elongate portion for being received in the humeral canal of a patient and a head receiving surface, the head receiving surface lying at an angle of greater than zero and less than 40 degrees relative to the elongate portion, each of the heads comprising consisting of a single unitary discoid body having first and second sides, a generally spherical segment shaped articulation surface for being received in and articulating in a socket in a patient's shoulder, said segment defining said first side surface of said discoid body, a generally planar stem engaging surface constructed and configured to lie adjacent the head receiving surface on the stem, the stem engaging surface and the head receiving surface lying generally in the same plane and being rotatable relative to each other, said stem engaging surface defining the second side of said discoid body, said first and second sides of the discoid body being spaced from each other by a central portion that defines a discoid circumference having a diameter, the central portion being generally wedge shaped for disposing the articulation surface at an angle of from greater than zero and less than about forty degrees from the plane in which the head receiving surface of the stem lies when the head is positioned thereon.

4. The prosthesis of claim 3 wherein the stem defines a frustoconical pin having a tapered outer surface and the head defines a recess having tapered walls for receiving the frustoconical pin, the taper of the walls and the taper of the outer surface of the pin form an interference fit to lock the head from rotation relative to the stem when the head is pressed toward the head receiving surface of the stem.

* * * * *